United States Patent [19]
Humayun et al.

[11] Patent Number: 5,935,155
[45] Date of Patent: Aug. 10, 1999

[54] VISUAL PROSTHESIS AND METHOD OF USING SAME

[75] Inventors: Mark S. Humayun, Baltimore; Eugene de Juan, Jr., Phoenix, both of Md.; Robert J. Greenberg, Los Angeles, Calif.

[73] Assignee: John Hopkins University, School of Medicine, Baltimore, Md.

[21] Appl. No.: 09/041,933

[22] Filed: Mar. 13, 1998

[51] Int. Cl.$^6$ .................................................. A61N 1/36
[52] U.S. Cl. ............................................................. 607/54
[58] Field of Search ................................ 607/53, 54, 116

[56] References Cited

U.S. PATENT DOCUMENTS

| | | | |
|---|---|---|---|
| 4,628,933 | 12/1986 | Michelson | 607/53 |
| 4,664,117 | 5/1987 | Beck | 128/420 |
| 4,793,353 | 12/1988 | Borkan | 607/54 |
| 4,918,745 | 4/1990 | Hutchinson | 455/41 |
| 4,979,508 | 12/1990 | Beck | 128/419 |
| 5,016,633 | 5/1991 | Chow | 128/419 |
| 5,024,223 | 6/1991 | Chow | 128/419 |
| 5,109,844 | 5/1992 | de Juan, Jr. et al. | 128/419 |
| 5,147,284 | 9/1992 | Fedorov et al. | 600/9 |
| 5,159,927 | 11/1992 | Schmid | 607/53 |
| 5,397,350 | 3/1995 | Chow et al. | 623/4 |
| 5,411,540 | 5/1995 | Edell et al. | 607/53 |
| 5,476,494 | 12/1995 | Edell et al. | 607/116 |
| 5,522,864 | 6/1996 | Wallace et al. | 607/53 |
| 5,554,187 | 9/1996 | Rizzo, III | 632/6 |
| 5,556,423 | 9/1996 | Chow et al. | 607/54 |
| 5,575,813 | 11/1996 | Edell et al. | 607/116 |
| 5,597,381 | 1/1997 | Rizzo, III | 623/4 |
| 5,674,263 | 10/1997 | Yamamoto et al. | 607/54 |

FOREIGN PATENT DOCUMENTS

| | | | |
|---|---|---|---|
| 2016276 | 9/1979 | United Kingdom | 607/53 |
| PCT/US96/ 08734 | 12/1996 | WIPO | A61N 1/05 |
| PCT/US96/ 13277 | 2/1997 | WIPO | A61F 2/16 |

OTHER PUBLICATIONS

Investigative Opthalmology & Visual Science pamphlet, Mar. 15, 1997, vol. 38, No. 4.
Clinical Sciences Magazine, Jan. 1996 issue, vol. 114, pp. 40–46, entitled Visual Perception Elicited by Electrical Stimulation of Retina in Blind Humans.
Publication entitled "Selective electrical stimulation of retinal neurons by varying stimulus pulse duration", dated Jul. 28, 1997.
Publication entitled "A Computational Model of Electrical Stimulation of the Retinal Ganglion Cell", dated Jun. 11, 1996.
Publication entitled "Dual Unit Visual Intraocular Prosthesis" for IEEE/EMBS, 19$^{th}$ International Conference, Oct. 30–Nov. 2, 1997, pp. 2303–2306.
Publication entitled "Electrode geometry design for a retinal prosthesis".

*Primary Examiner*—William E. Kamm
*Attorney, Agent, or Firm*—Leydig, Voit & Mayer, Ltd.

[57] ABSTRACT

A visual prosthesis comprises a camera for perceiving a visual image and generating a visual signal output, retinal tissue stimulation circuitry adapted to be operatively attached to the user's retina, and wireless communication circuitry for transmitting the visual signal output to the retinal tissue stimulation circuitry within the eye. To generate the visual signal output the camera converts a visual image to electrical impulses which are sampled to selecting an image at a given point in time. The sampled image signal is then encoded to allow a pixelized display of it. This signal then is used to modulate a radio frequency carrier signal. A tuned coil pair having a primary and a secondary coil are used to transmit and receive the RF modulated visual signal which is then demodulated within the eye. The retinal stimulation circuitry includes a decoder for decoding the visual signal output into a plurality of individual stimulation control signals which are used by current generation circuitry to generate stimulation current signals to be used by an electrode array having a plurality of electrodes forming a matrix. The intraocular components are powered from energy extracted from the transmitted visual signal. The electrode array is attached to the retina via tacks, magnets, or adhesive.

25 Claims, 7 Drawing Sheets

VISUAL PROSTHESIS AND METHOD OF USING SAME

TECHNICAL FIELD OF THE INVENTION

This invention relates to medical ocular devices and methods, and more particularly to intraocular electrical retinal stimulation for phosphene generation in a visual prosthesis device and method of using same.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concepts of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthesis devices were large, bulky and could not produce adequate simulated vision to truly aid the visually impaired.

As intraocular surgical techniques advanced, however, it became possible to apply a more focused stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

One such device is described in U.S. Pat. No. 4,628,933, issued to Michelson on Dec. 16, 1986, for a METHOD AND APPARATUS FOR VISUAL PROSTHESIS. The Michelson '933 apparatus includes an array of photosensitive devices on its surface which are connected to a plurality of electrodes positioned on the opposite surface of the device to stimulate the retina. These electrodes are disposed to form an array similar to a "bed of nails" having conductors which impinge directly on the retina to stimulate the retinal cells. The Michelson '933 device is powered by a separate circuit through electromagnetic or radio frequency induction. To receive this energy, an inductor is included with the Michelson '933 device either wound on the periphery of the device or formed on one of the surfaces through photolithographic circuit techniques. The induced signal is then rectified and filtered to power the circuit elements.

Such a device, however, increases the possibility of retinal trauma by the use of its "bed of nails" type electrodes which impinge directly on the retinal tissue. Additionally, by including the photosensitive elements integral with the implanted device within the eye, the processing of the perceived image is quite limited. It is first limited by the quality of the lens of the patient's eye and her ability to focus that lens. If the lens is occluded by cataracts or otherwise not clear, it will need to be replaced to allow proper operation of the prosthesis. Likewise, prescription glasses or contact lenses may be required to focus the image on the prosthesis for patients who would otherwise be near or far sighted.

The Michelson '933 device is also limited by the physical size available within the ocular cavity. Since this cavity is small and since the device must be supported by the retinal tissue itself, the amount of image processing circuitry which can be included therein is limited. Furthermore, the amount of image processing circuitry is also limited by the power availability and utilization requirements within the ocular cavity. As a result of these limiting factors, the Michelson '933 device does not include any image processing circuitry other than common signal amplifiers which simply tune the responses to the frequency response bandwidth of the retinal neurons, to shape the output waveform in a charge-balanced square wave, and trim the voltage and current output to acceptable levels for the neurons.

BRIEF SUMMARY OF THE INVENTION

In view of the above, it is therefore an object of the instant invention to overcome at least some of these and other known problems existing in the art. More particularly, it is an object of the instant invention to provide a new and improved visual prosthesis. Specifically, it is an object of the instant invention to provide a visual prosthesis which will at least partially restore vision in cases where blindness is caused by photoreceptor degenerative retinal diseases. It is a further objective of the instant invention to provide a visual prosthesis which provides a level of functional vision which will improve a patient's mobility and enable reading. Additionally, it is an object of the instant invention to provide such a visual prosthesis which can be worn during routine daily activities and which is aesthetically acceptable to the patient. Furthermore, it is an object of the instant invention to provide a method of restoring vision.

In view of these objectives, it is a feature of the visual prosthesis of the instant invention to provide both intra-ocular and extra-ocular components to maximize the visual quality produced and minimize the retinal effect caused by the visual prosthesis. It is a further feature of the instant invention to provide a means of transmitting the visual signal of the perceived environment from the extra-ocular components to the intra-ocular components without physical contact therebetween. Additionally, it is a feature of the instant invention to extract the required power for the intra-ocular components from the visual signal without the need for a separate power signal transmission. Furthermore, it is a feature of the instant invention to provide a visual prosthesis whose intra-ocular electrodes do not pierce the retina.

Therefore, in accordance with the above objectives and features, it is an aspect of the instant invention to provide a visual prosthesis having an extra-ocular image capturing and encoding element, and a radio frequency based transmission element. It is a further aspect of the instant invention to provide an intra-ocular stimulating electrode on the surface of the retina. In accordance with another aspect of the instant invention, a radio frequency receiving, decoding, and demultiplexing element is provided to receive the radio frequency transmitted visual signals. An aspect of one embodiment of the instant invention includes providing the radio frequency receiving, decoding, and demultiplexing element intra-ocular, while another aspect of another embodiment includes providing the radio frequency receiving, decoding, and demultiplexing element extra-ocular.

An embodiment of the visual prosthesis of the instant invention comprises a camera for converting a visual image to electrical impulses, image sampling circuitry for selecting an image at a given point in time, and encoder circuitry for encoding the selected image to allow a pixelized display of it. A signal corresponding to the selected image is then used to modulate a radio frequency carrier signal so that it can be transmitted into the eye by a tuned coil pair having a primary and a secondary coil.

A demodulator circuit is coupled to the secondary coil for extracting the visual signal output from the radio frequency carrier signal. A decoder is coupled to the demodulator for decoding the visual signal output into a plurality of individual stimulation control signals which are coupled to current generation circuitry which generates stimulation current signals in response. An electrode array has a plurality of electrodes which are operatively coupled to the current generation circuitry means. The electrodes stimulate the retinal tissue in response to these individual stimulation control signals.

A method of at least partially restoring vision to users who suffer from photoreceptor degenerative retinal conditions of the eye is included and comprises the steps of: a) perceiving a visual image and producing a visual signal output in response thereto; b) wirelessly transmitting the visual signal output into the eye; and c) stimulating retinal tissue of the user in accordance with the visual signal output.

These and other aims, objectives, and advantages of the invention will become more apparent from the following detailed description while taken into conjunction with the accompanying drawings.

While the invention is susceptible of various modifications and alternative constructions, certain illustrative embodiments thereof have been shown in the drawings and will be described below in detail. It should be understood, however, that there is no intention to limit the invention to the specific forms disclosed, but on the contrary, the intention is to cover all modifications, alternative constructions, methods, and equivalents falling within the spirit and scope of the invention as defined by the appended claims.

DETAILED DESCRIPTION OF THE PREFERRED EMBODIMENT

As discussed briefly above, the apparatus of the instant invention is a medical device which will at least partially restore vision in cases where blindness is caused by photoreceptor degenerative retinal diseases such as retinitis pigmentosa and age related macular degeneration which affect millions of people worldwide. The partial restoration of vision is intended to improve the patient's mobility and enable at least large print reading, and thus provide an increased sense of independence. Briefly, visual perception is achieved by converting an image of the scene before the patient into a series of electrical pulses that are mapped onto the retina by electrically stimulating the viable nerve cells beyond the dysfunctional photoreceptors. It is therefore a goal of the instant invention to provide a level of functional vision in a package that can be worn during routine daily activities and is aesthetically acceptable to the patient. The entire system of the instant invention is contained in a portable body worn package which functions without the use of implanted batteries or connector penetrations of the eye. The intraocular portions of the visual prosthesis of the instant invention are designed to be implanted in the patient's eye using standard ophthalmic surgical techniques.

Specifically, therefore, a visual prosthesis in accordance with a preferred embodiment of the instant invention comprises a means for perceiving a visual image which produces a visual signal output in response thereto, a retinal tissue stimulation means adapted to be operatively attached to a retina of a user, and a wireless visual signal communication means for transmitting the visual signal output to the retinal tissue stimulation means. Preferably, the means for perceiving a visual image comprises a camera means for converting a visual image to electrical impulses, image sampling means coupled to the camera means for selecting an image at a given point in time, and encoder means coupled to the image sampling means for encoding the selected image to allow a pixelized display thereof.

Additionally, in a preferred embodiment of the instant invention, the retinal tissue stimulation means comprises a decoder means responsive to the visual signal output for decoding the visual signal output into a plurality of individual stimulation control signals, current generation circuitry means coupled to the decoder means and responsive to the plurality of individual stimulation control signals for generating stimulation current signals, and an electrode array having a plurality of electrodes operatively coupled to the current generation circuitry means. These electrodes are responsive to the individual stimulation control signals, and generate stimulation pulses sufficient to stimulate retinal tissue.

Furthermore, in a preferred embodiment of the instant invention, the electrode array further comprises attachment means adapted for attaching the electrode array to the retina of a user. In an embodiment, the electrode array defines at least one mounting aperture therein, and the attachment means comprises at least one retinal tack positioned within the at least one mounting aperture. Alternatively, the electrode array includes an outer surface edge defining at least two scalloped portions therein, and the attachment means comprises a retinal tack positioned within each of the scalloped portions. In a further alternate embodiment, the electrode array includes at least a first magnet attached thereto, and the attachment means comprises a second magnet adapted to be attached on the outside of the sclera of a user opposite a desired point of attachment of the electrode array on the retina. In yet a further embodiment, the attachment means comprises adhesive placed on a surface of said electrode array to be attached to the retina.

In a further embodiment of the instant invention, the wireless visual signal communication means comprises a carrier generator means for generating a radio frequency carrier signal, a modulator means responsive to the radio frequency carrier signal and to the visual signal output for modulating the radio frequency carrier signal by the visual signal output, producing a radio frequency modulated image signal. Additionally, this embodiment includes a tuned coil pair having a primary and a secondary coil. The primary coil is operatively coupled to the modulator means to transmit the radio frequency modulated image signal. The secondary coil is tuned to receive the radio frequency modulated image signal. A demodulator means is coupled to the secondary coil for extracting the visual signal output from the radio frequency carrier signal.

A preferred embodiment of the instant invention further comprising power supply means coupled to the secondary coil for powering the retinal tissue stimulation means and the demodulator means. This is accomplished preferably by extracting energy from the radio frequency modulated image signal. The power supply means rectifies the radio frequency carrier signal from the radio frequency modulated image signal received by said secondary coil to produce the dc power output to power the retinal tissue stimulation means and the demodulator means.

A preferred method of at least partially restoring vision to users who suffer from photoreceptor degenerative retinal conditions of the eye, therefore, comprises the steps of perceiving a visual image and producing a visual signal output in response thereto, wirelessly transmitting the visual signal output into the eye, and stimulating retinal tissue of the user in accordance with the visual signal output. Preferably, the step of perceiving a visual image and producing a visual signal output in response thereto comprises the steps of converting a visual image to electrical impulses, sampling the electrical impulses corresponding to an image at a given point in time, and encoding the selected image to allow a pixelized display thereof.

Additionally, preferably the step of wirelessly transmitting the visual signal output into the eye comprises the steps of generating a radio frequency carrier signal, modulating the radio frequency carrier signal by the visual signal output to produce a radio frequency modulated image signal, transmitting the radio frequency modulated image signal, receiving the radio frequency modulated image signal, and extracting the visual signal output from the radio frequency carrier signal. Moreover, in a preferred embodiment the step of stimulating retinal tissue of the user in accordance with the visual signal output comprises the steps of decoding the visual signal output into a plurality of individual stimulation control signals, generating stimulation current signals, and applying stimulation to the retinal tissue in accordance with the stimulation current signals.

Figure 1:
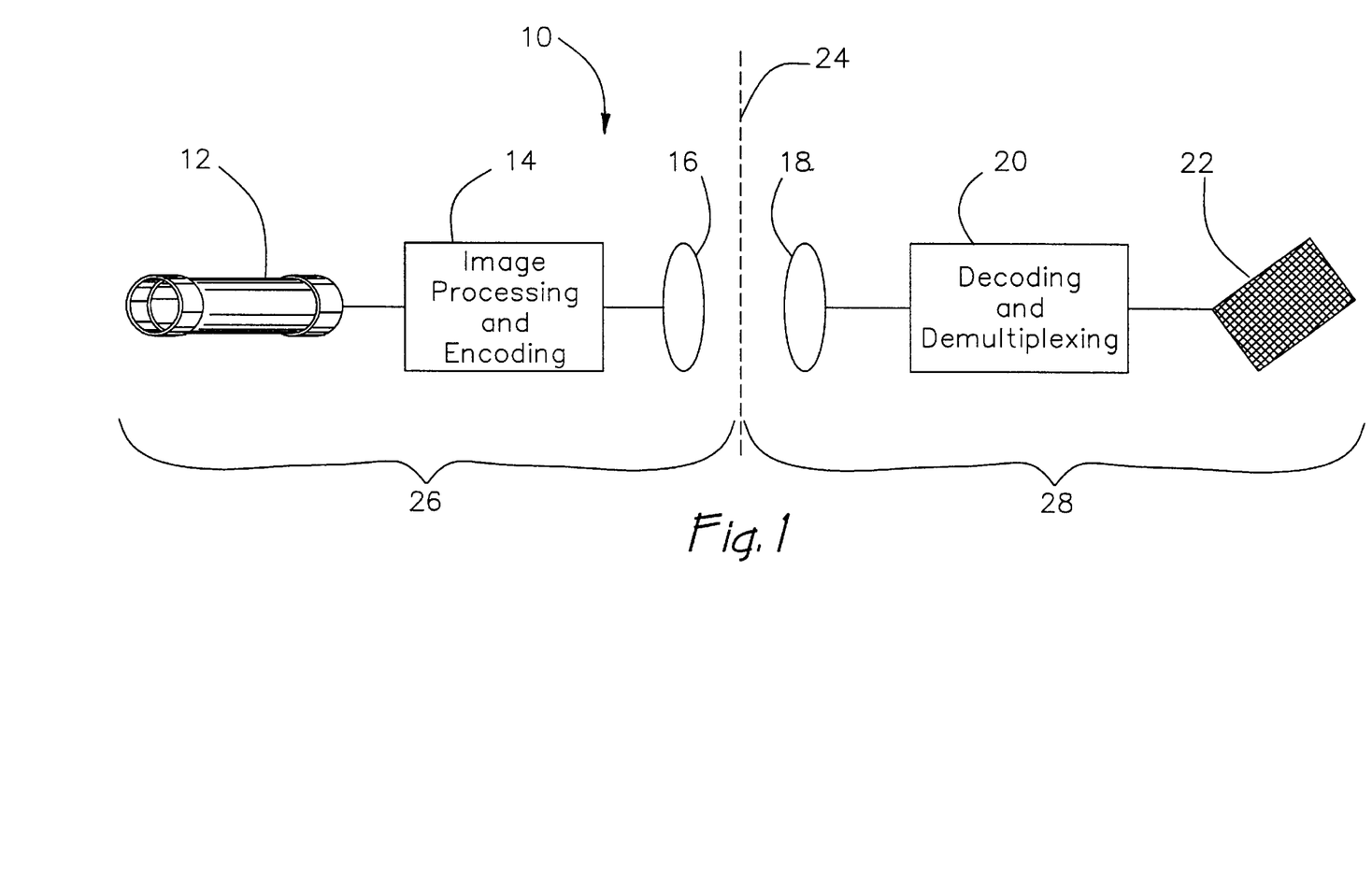
FIG. 1 is a simplified schematic block diagram of a visual prosthesis in accordance with an embodiment of the instant invention.

In an exemplary embodiment of the above described invention illustrated in block diagram form in FIG. 1, a visual prosthetic device, illustrated as retinal prosthesis 10, includes an image capturing element, such as a standard charge coupled device (CCD) camera 12, whose visual signal output is processed and encoded in circuit block 14. This processed and encoded image signal is then transmitted via primary coil 16 as a radio frequency encoded image signal. A secondary coil 18 receives the radio frequency encoded image signal and passes it to the decoding and demultiplexing circuit block 20. This circuit block 20 then communicates the decoded image signal to an electrode array 22 which stimulates the retinal cells to produce phosphenes in a pattern to simulate vision.

It should be noted that the dashed line 24 in FIG. 1 is included to separate the image acquiring and transmitting portion 26 from the image receiving and stimulation portion 28 of the visual retinal prosthesis 10, and may or may not indicate the separation of the extra-ocular region from the intra-ocular region as will be described more fully below with reference to FIGS. 4–6. It should also be noted that while the figures illustrate the use of a CCD camera, the scope of the invention is not so limited but includes other technologies of image acquisition equipment such as video cameras, digital cameras, CMOS cameras, etc.

Figure 2:
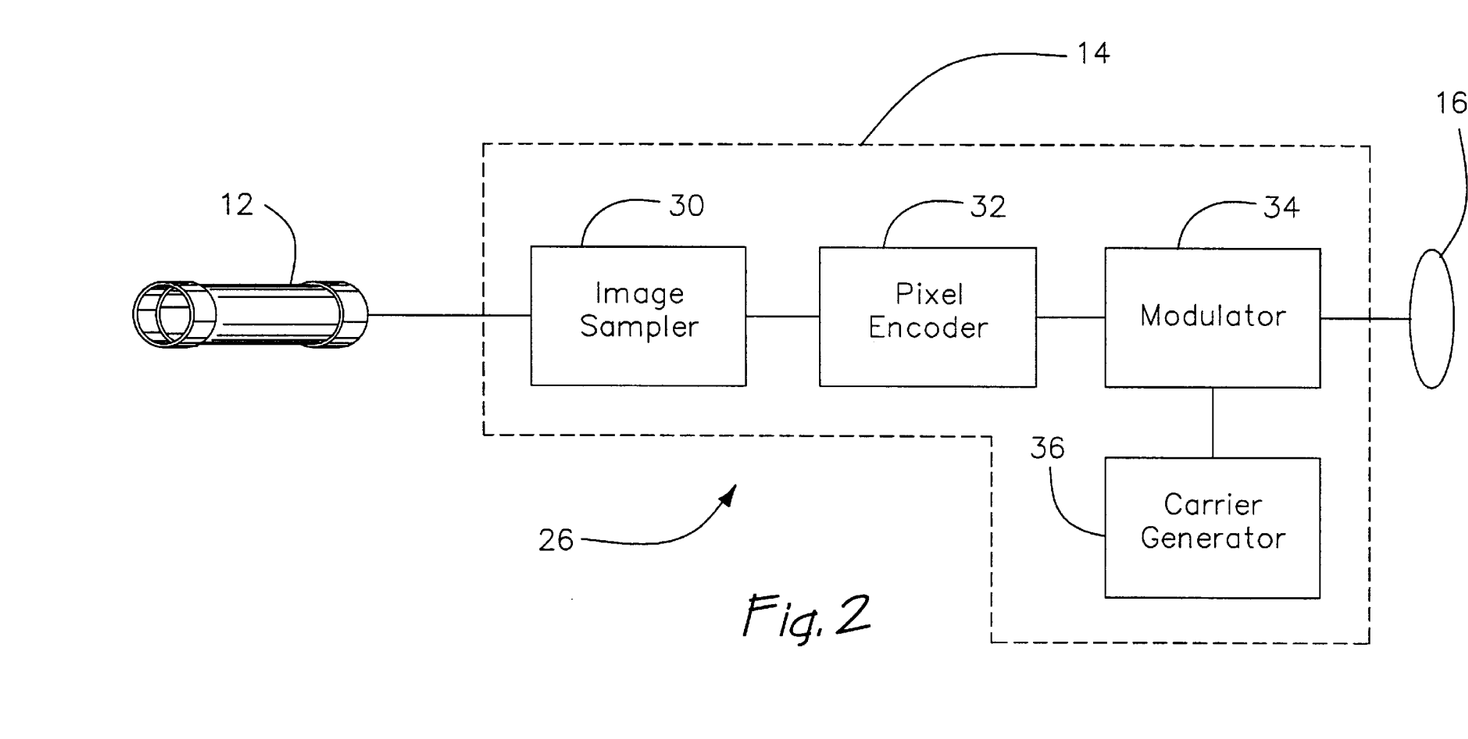
FIG. 2 is an expanded schematic block diagram of visual acquiring, encoding, and radio frequency transmission components of an embodiment of the visual prosthesis of the instant invention.

The image acquiring and transmitting portion 26 of the visual prosthesis of the instant invention is illustrated in greater detail in FIG. 2, and reference is now made thereto. As may be observed from this figure, the image signal captured by the camera 12 is output to an image sampler circuit 30, and this sampled image is passed to the pixel encoder 32. Once this sampled image signal is properly encoded, it is passed to the signal modulator 34 which uses it to modulate a radio frequency carrier signal generated by the carrier generator 36. This radio frequency modulated image signal is then transmitted via the primary coil 16.

The encoding scheme is optimized for the target image resolution which is determined by the size of the implanted electrode array, as discussed more fully below. The encoded information includes such parameters as the magnitude, timing, and sequence of the stimulation pulses which will be generated by the array to simulate the image through retinal stimulation. The modulation technique is consistent with the data rate, and maximizes the fidelity of the recovered information over the intended transmission path.

Figure 3:
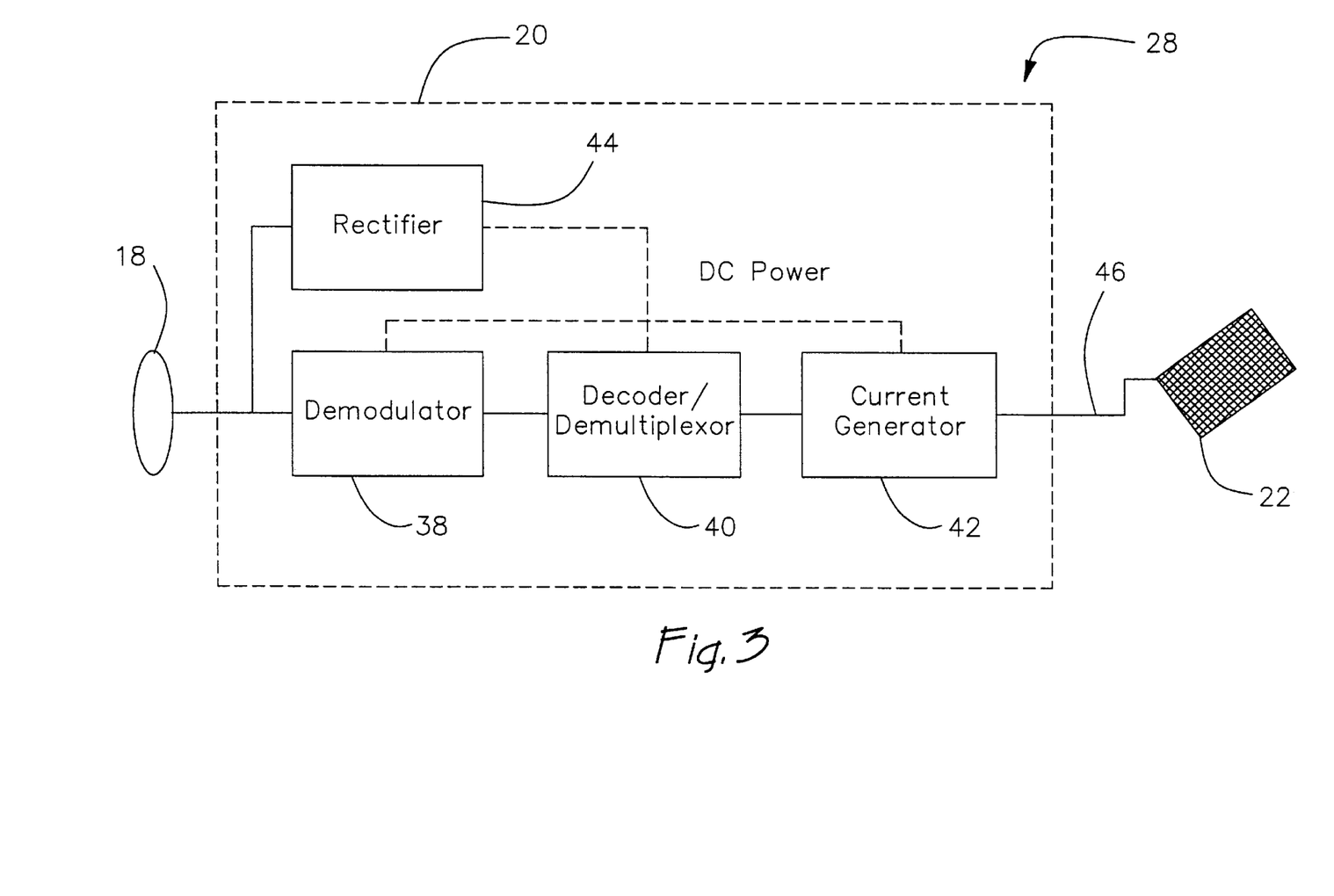
FIG. 3 is an expanded schematic block diagram of radio frequency visual signal receiving, decoding, and retinal stimulation components of an embodiment of the visual prosthesis of the instant invention.

The radio frequency modulated image signal is received by the image receiving and stimulation portion 28 of the visual prosthesis, as illustrated in greater detail in FIG. 3. Once this signal is received by the secondary coil 18, it is passed to the demodulator 38 where the carrier signal is removed from the encoded image signal. The encoded image signal is then passed to a decoder/demultiplexer 40 which in turn outputs the image information to a current generator 42 which drives the individual electrodes of the electrode array 22. The electric power for this image receiving and stimulation portion 28 of the visual prosthesis is derived from the energy contained in the carrier signal through rectifier 44. This carrier signal is rectified to provide the direct current to power the implanted electronics and generate the stimulation pulses. In this way a separate power transmission signal is not required.

The image receiving and stimulation portion 28 of the visual prosthesis serves to demodulate and decode the stimulation information and generate the proper stimulation pulses which are transmitted to the electrode array 22 implanted on the retina. The decoded transmission is used to determine the characteristics of the stimulation pulse and where this pulse is applied on the electrode array 22. The pulses are transferred by means of a miniature ribbon cable 46 that lies within the intraocular cavity, or by other appropriate means such as, for example, fiberoptic cable.

Figure 4:
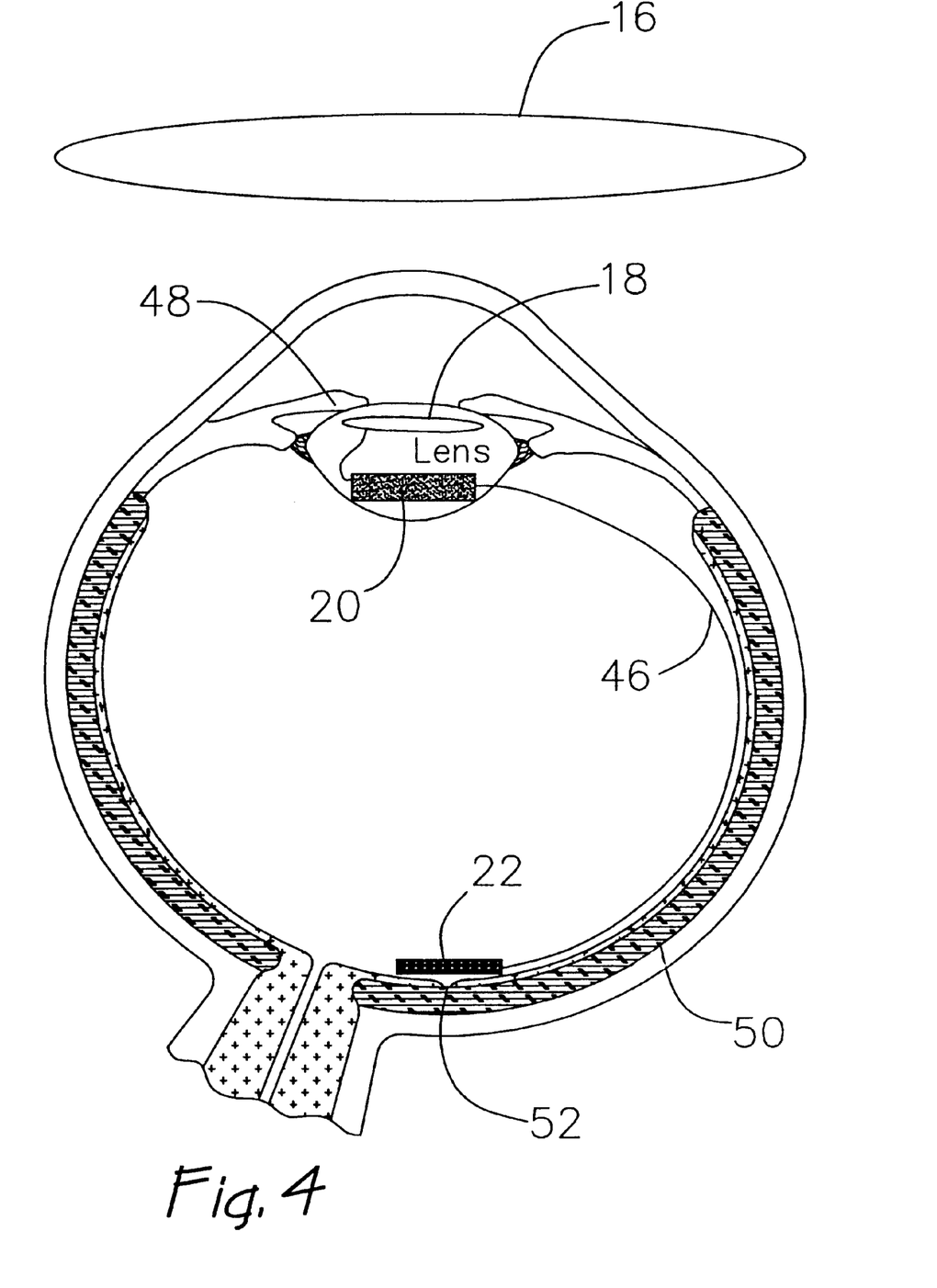
FIG. 4 is a simplified cross-sectional view of an embodiment of the visual prosthesis of the instant invention as implanted within the eye.
Figure 8:
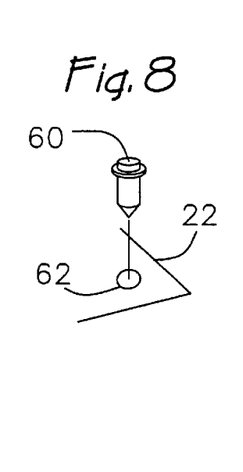
FIG. 8 is a partial schematic view of a section of an intra-ocular stimulation electrode array illustrating attachment details thereof in accordance with an aspect of an embodiment of the visual prosthesis of the instant invention.

One embodiment of the physical implantation of the visual prosthesis of the instant invention is illustrated in FIG. 4 to which reference is now made. As discussed above, the primary coil 16 is used to transmit the radio frequency encoded image signal to the secondary coil 18. This primary coil is located preferably either in an eyeglass lens, frame, or in a soft contact lens. This coil 16 is used to inductively couple the radio frequency encoded image signal to the secondary coil 18 which, in this embodiment, is implanted behind the iris 48. This secondary coil 18 is coupled to and collocated with the decoding/demultiplexing circuitry 20. The small ribbon cable 46 is located along the interior wall of the eye and couples the circuitry 20 to the electrode array 22 which is placed on the retina 50 near the fovea 52. Alternatively, the circuitry 20 can be integrated with the electrode array 22, in which case only a small wire from the secondary coil 18 is needed to couple the visual signal to the combined circuitry and array (not illustrated). The details of the attachment mechanisms for securing the electrode array 22 to the retina 50 will be described in detail below with reference to FIGS. 8–10.

Figure 5:
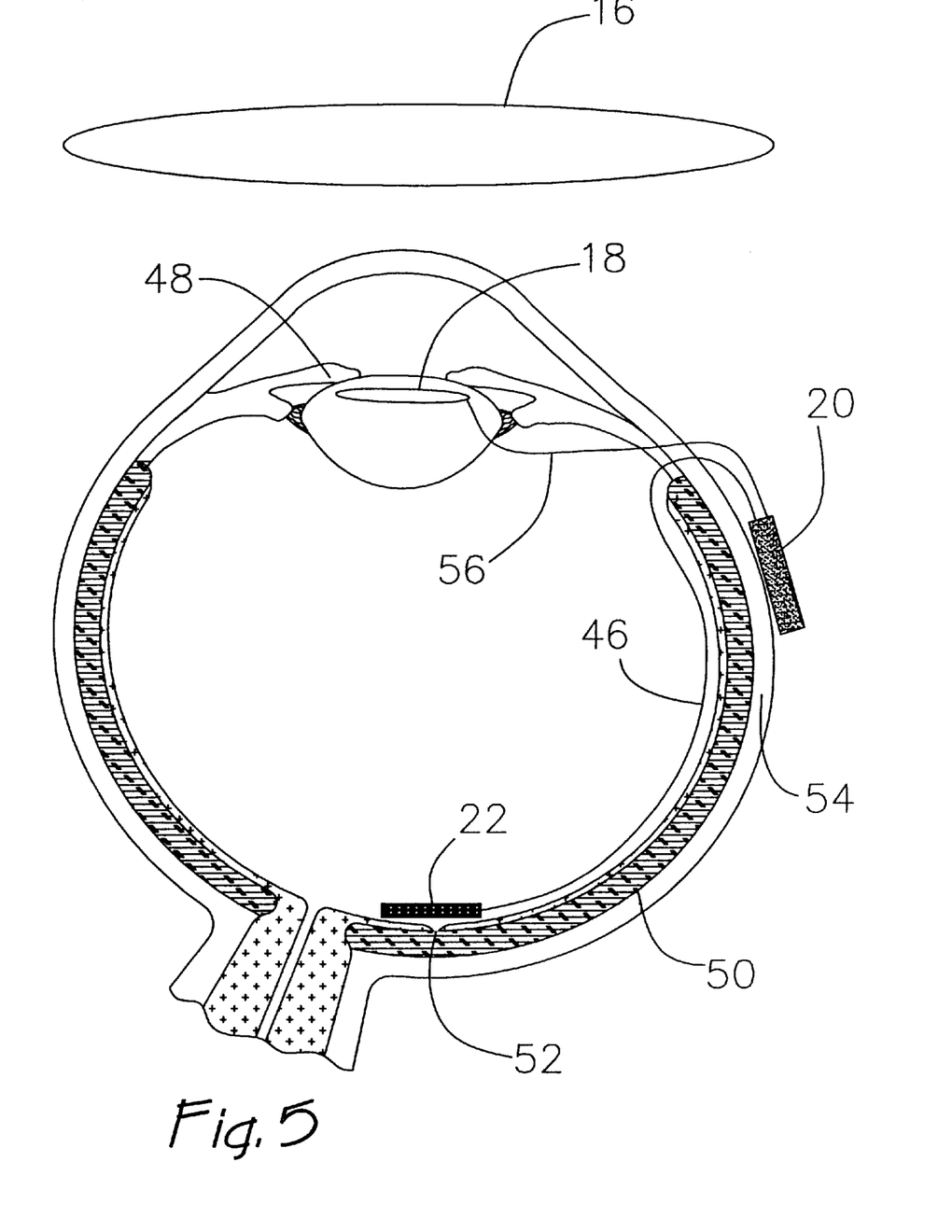
FIG. 5 is a simplified cross-sectional view of an alternate embodiment of the visual prosthesis of the instant invention as implanted within the eye.

In an alternate embodiment of the instant invention illustrated in FIG. 5, the decoding/demultiplexing circuitry 20 is no longer collocated with the secondary coil 18 behind the iris 48, but is instead attached to the outside of the sclera 54. The attachment may be by suturing or other appropriate means. In this embodiment the decoding/demultiplexing circuitry 20 is placed in a hermetically sealed package and is coupled to the secondary coil by a small wire 56 which pierces the sclera 54. The small ribbon cable 46 coupling the decoding/demultiplexing circuitry 20 to the electrode array 22 mounted on the retina 50 also pierces the sclera 54.

Figure 6:
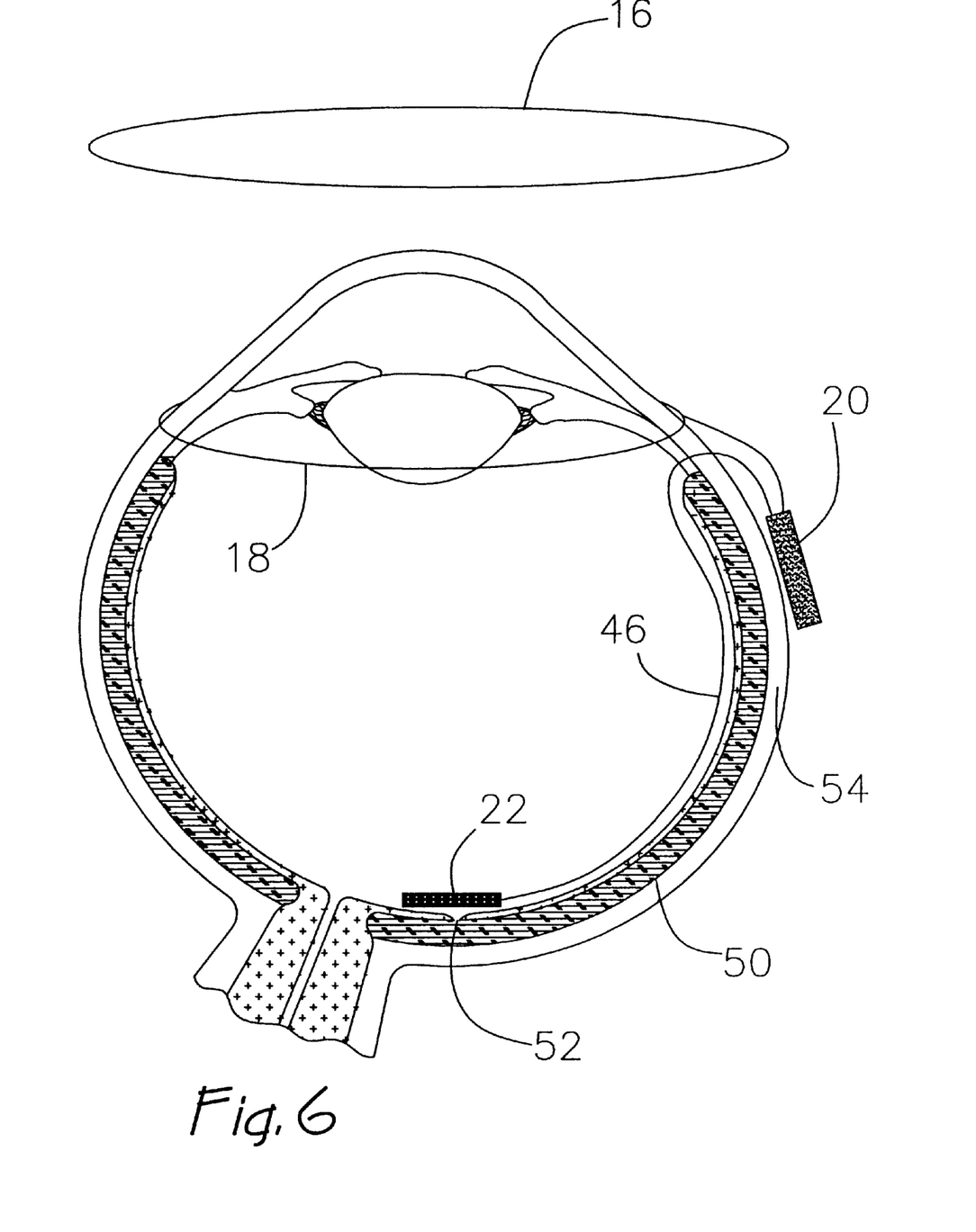
FIG. 6 is a simplified cross-sectional view of a further alternate embodiment of the visual prosthesis of the instant invention as implanted within the eye.

In a further alternate embodiment of the instant invention, as illustrated in FIG. 6, the secondary coil may also be attached to the sclera 54 instead of being implanted within the eye. As with the decoding/demultiplexing circuitry 20, the attachment of the secondary coil 18 to the sclera 54 may be by suturing or other appropriate means. In this way, only the small ribbon cable 46 which attaches the decoding/demultiplexing circuitry 20 to the electrode array 22 mounted on the retina 50 is required to pierce the sclera 54. The extra-ocular attachment of the decoding/demultiplexing circuitry 20 allows increased access to this circuitry which eases the replacement or updating of these components.

Figure 7:
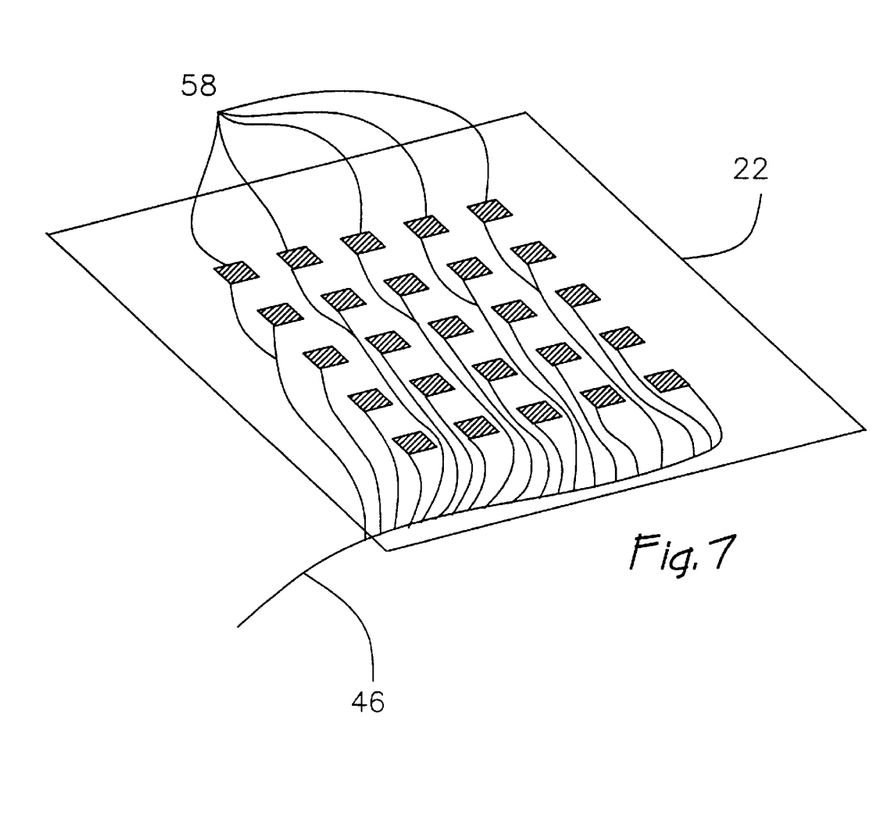
FIG. 7 is a simplified schematic view of an intraocular stimulation electrode array in accordance with an aspect of an embodiment of the visual prosthesis of the instant invention.

As discussed above, the electrode array 22, illustrated schematically in FIG. 7, is a biocompatible device which is mounted onto the surface of the retina near the fovea. This array 22 can either be a passive element that only serves to transfer the charge in the stimulation pulses to the retinal tissue, or an active network that can control the selection of the stimulation sites using information encoded in its input. The stimulation sites 58 in the array are spaced to provide a level of visual acuity consistent with the ability of the patient to discriminate the activation of adjacent sites. The stimulation sites 58 are composed of a material designed to maximize the transfer of charge between the electrode and the surrounding tissue. While the array 22 illustrated in FIG. 7 has only a 5×5 array of stimulation sites, this number may be increased or decreased. If the size of the array 22 increases, it is preferable that the array 22 be flexible to allow surface contact with all appropriate areas of the retina. An electrode design which is compatible with electrode array 22 of the instant invention is disclosed in U.S. Pat. No. 5,109,844, issued to de Juan, Jr. et al. on May 5, 1992, for RETINAL MICROSTIMULATION, the teachings and disclosure of which are hereby incorporated by reference.

The attachment of the electrode array to the surface of the retina is accomplished using any suitable method. In one embodiment illustrated in FIG. 8, a mechanical fixation device, such as titanium tack 60 commonly employed to aid in retinal re-attachment by holding the detached section of retina against the choroid, is used. The tack 60 is passed through a circular hole 62 in each corner of the body of the array 22 and holds the array in place by piercing the retina, choroid, and sclera. As an alternative to the tack 60, suturing may also serve as the mechanical fixation device.

Figure 9:
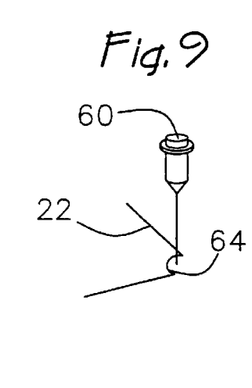
FIG. 9 is a partial schematic view of a section of an intra-ocular stimulation electrode array illustrating attachment details thereof in accordance with an aspect of an alternative embodiment of the visual prosthesis of the instant invention.

In an alternate embodiment, as illustrated in FIG. 9, the array may be secured to the retina by placing the tack 60 into a scalloped portion illustrated as a semicircular notch 64 in each corner of the array 22, and the resulting compression of the array 22 holds it in place. This method of attachment offers the advantage of easier replacement since the tack 60 does not penetrate the body of the array.

Figure 10:
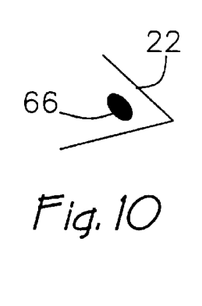
FIG. 10 is a partial schematic view of a section of an intra-ocular stimulation electrode array illustrating attachment details thereof in accordance with an aspect of a further alternative embodiment of the visual prosthesis of the instant invention.

A less intrusive alternate method of attaching the array 22 to the retina is illustrated in the alternate embodiment of FIG. 10. This embodiment utilizes inert miniature rare earth magnets 66 which are embedded into each corner of the silicone array 22 during casting. A second set of magnets (not shown) are sewn onto the outside of the eye directly across from the desired position of the array 22. The magnetic attraction between the intraocular magnets 66 in the array 22 and the magnets sewn on the outside of the eye serves to hold the array 22 in place. This method obviates the need to pierce the eye wall with a tack and allows for easier replacement of the array.

An alternate embodiment of the instant invention utilizes a medically approved adhesive, such as cyanoacrylate or other appropriate adhesive, to secure the array to the retina. In this embodiment, the adhesive is applied to the edges of the array prior to its final placement on the retina. A temporary air pocket is then created in the vitreous to allow the adhesive to cure.

In a preferred embodiment of the visual prosthesis of the instant invention, the materials utilized in the components which are part of the retinal implant are those used in current day cochlear implants. It should be noted, however, that designation of such materials does not limit the scope of the invention as other, possibly better and more appropriate materials may be approved for intraocular implantation. In a preferred embodiment, the packaging for the implanted electronics is preferably titanium covered by silicone. The secondary coil is preferably made of platinum and also embedded in silicone. In this embodiment the electrode array is preferably composed of platinum wires within a silicone matrix. All of these materials have been approved by the FDA for intraocular use and exhibit proper electrical and biological characteristics for use in such a visual prosthesis.

Numerous modifications and alternative embodiments of the invention will be apparent to those skilled in the art in view of the foregoing description. Accordingly, this description is to be construed as illustrative only and is for the purpose of teaching those skilled in the art the best mode for carrying out the invention. The details of the structure and architecture may be varied substantially without departing from the spirit of the invention, and the exclusive use of all modifications which come within the scope of the appended claims is reserved.

What is claimed is:

1. A visual prosthesis, comprising:

means for perceiving a visual image, said means producing a visual signal output in response thereto;

retinal tissue stimulation means adapted to be operatively attached to a retina of a user; and wireless visual signal communication means for transmitting said visual signal output to said retinal tissue stimulation means.

2. The visual prosthesis of claim 1, wherein said means for perceiving a visual image comprises:

camera means for converting a visual image to electrical impulses;

image sampling means coupled to said camera means for selecting an image at a given point in time; and encoder means coupled to said image sampling means for encoding said selected image to allow a pixelized display thereof.

3. The visual prosthesis of claim 1, wherein said retinal tissue stimulation means comprises:

decoder means responsive to said visual signal output for decoding said visual signal output into a plurality of individual stimulation control signals;

current generation circuitry means coupled to said decoder means and responsive to said plurality of individual stimulation control signals for generating stimulation current signals; and an electrode array having a plurality of electrodes operatively coupled to said current generation circuitry means, said electrodes being responsive to said individual stimulation control signals to generate stimulation pulses sufficient to stimulate retinal tissue.

4. The visual prosthesis of claim 3, said electrode array further comprising attachment means adapted for attaching said electrode array to the retina of a user.

5. The visual prosthesis of claim 4, wherein said electrode array defines at least one mounting aperture therein, and wherein said attachment means comprises at least one retinal tack positioned within said at least one mounting aperture.

6. The visual prosthesis of claim 4, wherein said electrode array includes an outer surface edge defining at least two scalloped portions therein, and wherein said attachment means comprises a retinal tack positioned within each of said scalloped portions.

7. The visual prosthesis of claim 4, wherein said electrode array includes at least a first magnet attached thereto, and wherein said attachment means comprises a second magnet adapted to be attached on the outside of the sclera of a user opposite a desired point of attachment of said electrode array on the retina.

8. The visual prosthesis of claim 4, wherein said attachment means comprises adhesive placed on a surface of said electrode array to be attached to the retina.

9. The visual prosthesis of claim 1, wherein said wireless visual signal communication means comprises:

a carrier generator means for generating a radio frequency carrier signal;

modulator means responsive to said radio frequency carrier signal and to said visual signal output for modulating said radio frequency carrier signal by said visual signal output, said modulator means producing a radio frequency modulated image signal;

a tuned coil pair having a primary and a secondary coil, said primary coil operatively coupled to said modulator means to transmit said radio frequency modulated image signal, said secondary coil being tuned to receive said radio frequency modulated image signal; and demodulator means coupled to said secondary coil for extracting said visual signal output from said radio frequency carrier signal.

10. The visual prosthesis of claim 9, further comprising power supply means coupled to said secondary coil for powering said retinal tissue stimulation means and said demodulator means by extracting energy from said radio frequency modulated image signal.

11. The visual prosthesis of claim 10, wherein said power supply means rectifies said radio frequency carrier signal from said radio frequency modulated image signal received by said secondary coil to produce a dc power output to power said retinal tissue stimulation means and said demodulator means.

12. A medical device to at least partially restore vision in users who suffer from photoreceptor degenerative conditions, comprising:

camera means for converting a visual image to electrical impulses;

image sampling means coupled to said camera means for selecting an image at a given point in time;

encoder means coupled to said image sampling means for encoding said selected image to allow a pixelized display thereof, said encoder means outputting a visual signal output;

a carrier generator means for generating a radio frequency carrier signal;

modulator means responsive to said radio frequency carrier signal and to said visual signal output for modulating said radio frequency carrier signal by said visual signal output, said modulator means producing a radio frequency modulated image signal;

a tuned coil pair having a primary and a secondary coil, said primary coil operatively coupled to said modulator means to transmit said radio frequency modulated image signal, said secondary coil being tuned to receive said radio frequency modulated image signal;

demodulator means coupled to said secondary coil for extracting said visual signal output from said radio frequency carrier signal;

decoder means coupled to said demodulator means and responsive to said visual signal output for decoding said visual signal output into a plurality of individual stimulation control signals;

current generation circuitry means coupled to said decoder means and responsive to said plurality of individual stimulation control signals for generating stimulation current signals; and an electrode array having a plurality of electrodes operatively coupled to said current generation circuitry means, said electrodes being responsive to said individual stimulation control signals to generate stimulation pulses sufficient to stimulate retinal tissue to generate phosphenes.

13. The medical device of claim 12, further comprising power supply means coupled to said secondary coil for powering said demodulator means, said decoder means, and said current generation circuitry means by extracting energy from said radio frequency modulated image signal.

14. The medical device of claim 13, wherein said electrode array is adapted for intraocular implantation.

15. The medical device of claim 14, wherein said secondary coil is adapted for intraocular implantation.

16. The medical device of claim 15, wherein said demodulator means, said decoder means, said current generation circuitry means, and said power supply means are adapted for intraocular implantation.

17. The medical device of claim 14, further comprising attachment means adapted for attaching said electrode array to retinal tissue of the user.

18. The medical device of claim 17, wherein said electrode array defines at least one mounting aperture therein, and wherein said attachment means comprises at least one retinal tack positioned within said at least one mounting aperture.

19. The medical device of claim 17, wherein said electrode array includes an outer surface edge defining at least two scalloped portions therein, and wherein said attachment means comprises a retinal tack positioned within each of said scalloped portions.

20. The medical device of claim 17, wherein said electrode array includes at least a first magnet attached thereto, and wherein said attachment means comprises a second magnet adapted to be attached on the outside of the sclera of a user opposite a desired point of attachment of said electrode array on the retina.

21. The medical device of claim 17, wherein said attachment means comprises adhesive placed on a surface of said electrode array to be attached to the retina.

22. A method of at least partially restoring vision to users who suffer from photoreceptor degenerative retinal conditions of the eye, comprising the steps of:

perceiving a visual image and producing a visual signal output in response thereto;

wirelessly transmitting the visual signal output into the eye;

stimulating retinal tissue of the user in accordance with the visual signal output.

23. The method of claim 22, wherein said step of perceiving a visual image and producing a visual signal output in response thereto comprises the steps of:

converting a visual image to electrical impulses;

sampling the electrical impulses corresponding to an image at a given point in time; and encoding said selected image to allow a pixelized display thereof.

24. The method of claim 22, wherein said step of wirelessly transmitting the visual signal output into the eye comprises the steps of:

generating a radio frequency carrier signal;

modulating said radio frequency carrier signal by said visual signal output to produce a radio frequency modulated image signal;

transmitting said radio frequency modulated image signal;

receiving said radio frequency modulated image signal; and extracting said visual signal output from said radio frequency carrier signal.

25. The method of claim 22, wherein said step of stimulating retinal tissue of the user in accordance with the visual signal output comprises the steps of:

decoding said visual signal output into a plurality of individual stimulation control signals;

generating stimulation current signals; and applying stimulation to the retinal tissue in accordance with the stimulation current signals.

* * * * *